(12) United States Patent
Shiraki et al.

(10) Patent No.: US 8,338,645 B2
(45) Date of Patent: Dec. 25, 2012

(54) METHOD FOR PRODUCING A β-ALKOXYPROPIONAMIDE

(75) Inventors: Yasushi Shiraki, Sodegaura (JP); Shigeru Matsuo, Sodegaura (JP); Toyozo Fujioka, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 522 days.

(21) Appl. No.: 12/526,530

(22) PCT Filed: Jan. 30, 2008

(86) PCT No.: PCT/JP2008/051332
§ 371 (c)(1),
(2), (4) Date: Aug. 10, 2009

(87) PCT Pub. No.: WO2008/102615
PCT Pub. Date: Aug. 28, 2008

(65) Prior Publication Data
US 2010/0076223 A1 Mar. 25, 2010

(30) Foreign Application Priority Data
Feb. 20, 2007 (JP) .................................. 2007-039383

(51) Int. Cl.
*C07C 231/02* (2006.01)
(52) U.S. Cl. ........................................................ 564/136
(58) Field of Classification Search .................... 564/136
See application file for complete search history.

(56) References Cited

U.S. PATENT DOCUMENTS 3,914,303 A 10/1975 Daniher et al.

FOREIGN PATENT DOCUMENTS

| JP | 49-66623 | 6/1974 |
| JP | 2-48559 | 2/1990 |
| JP | 2-83358 | 3/1990 |
| JP | 10-279545 | 10/1998 |
| JP | 2004-250353 | 9/2004 |
| JP | 2005-47885 | 2/2005 |

OTHER PUBLICATIONS

U.S. Appl. No. 13/133,683, filed Jun. 9, 2011, Shiraki, et al.
Edited by The Chemical Society of Japan, Shinjikken Kagaku Koza 14 Yuki Kagobutsu no Gosei to Hanno II, Maruzen Co., Ltd., Dec. 20, 1977, pp. 1147-1150.
Sandler, Karo/translated by Naoki Inamoto, et al., Kannoki Betsu Yuki Kagobutsu Goseiho I, Kabushiki Kaisha Hirokawa Shoten, Mar. 25, 1976, pp. 303-307.

*Primary Examiner* — Shailendra Kumar
(74) *Attorney, Agent, or Firm* — Oblon, Spivak, McClelland, Maier & Neustadt, L.L.P.

(57) ABSTRACT

A method for producing a β-alkoxypropionamide shown by the following formula (I) including the step of reacting a β-alkoxypropionic acid ester with an amine in the presence of a basic catalyst or in the presence of a basic catalyst and a polyol:

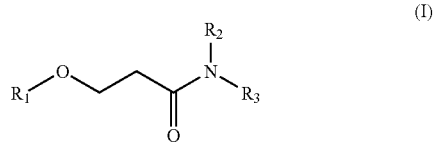

(I)

wherein $R_1$ is an alkyl group having 1 to 8 carbon atoms, and $R_2$ and $R_3$ are independently hydrogen, a methyl group, an ethyl group, a methoxy group, an ethoxy group, a methoxymethyl group or a glycidyl group.

16 Claims, No Drawings

METHOD FOR PRODUCING A β-ALKOXYPROPIONAMIDE

This application is a 371 of PCT/JP2008/051332, filed Jan. 30, 2008.

TECHNICAL FIELD

The invention relates to a method for producing a β-alkoxypropionamide. More particularly, the invention relates to a method for producing a β-alkoxypropionamide which comprising the step of reacting an alkoxypropionic acid ester with an amine.

BACKGROUND ART

Generally, an amino-based organic solvent has desired performance as a solvent or a detergent since it has improved solubility and is capable of being rinsed with water due to its property of being dissolved easily in water. For these reasons, an amino-based organic solvent can be used as a resist peeling agent, for example.

In recent years, there is a tendency that a conventional halogen-based solvent is replaced by an amide-based solvent since a halogen-based solvent may cause environment pollution as it destroys the ozone layer or the like, and also has strong toxicity. In addition, an amide-based solvent is expected to be used instead of a reproductive toxic compound such as NMP.

However, a method for synthesizing an amide-based solvent at a low cost has not yet been established. Under such circumstances, an inexpensive method for synthesizing an amide-based solvent which can be realized on the industrial scale has been awaited.

As the method for synthesizing an amide-based solvent at a low cost, a method in which an acrylic acid ester is used as a starting material can be given. Specifically, the following methods can be used. An alkoxypropionic acid ester is synthesized from an acrylic acid ester, and the resulting alkoxypropionic acid ester is directly amidized, or, an alkoxypropionic acid ester is once hydrolyzed to produce an alkoxyacrylic acid, and the resulting alkoxyacrylic acid is reacted with an amine to form a salt, followed by heat decomposition to allow an amide to be synthesized.

For example, Patent Document 1 discloses synthesis of β-alkoxy-N,N-dialkylpropionamide as an intermediate in a method for producing a N,N-dialkylpropionamide of an α,β-olefin-based unsaturated monocarboxylic acid which is used as a polymerizable monomer. Specifically, this is a method in which a β-alkoxypropionic acid ester and a dialkylamine are reacted in the presence of a polyol having two adjacent hydroxyl groups.

This method, however, requires a large amount of a polyol. In addition, in order to attain a high conversion ratio, it is necessary to conduct a reaction for a long period of time at high temperatures.

Patent Document 2 discloses a method in which an acrylic acid amide is reacted with an aliphatic monovalent alcohol having 1 to 4 carbon atoms. According to this method, synthesis can be performed under moderate conditions.

However, an acrylic acid amide is generally produced in three to four steps, as stated in Patent Document 2. In addition, an acrylic acid amide itself is expensive. Therefore, production cost is increased if a β-alkoxypropionamide is produced by this method.

In addition, a method is known in which dimethylamine is reacted with alkoxy acid chloride. For example, by reacting dimethylamine with 3-ethoxy-propionylchloride in the presence of a diethyl ether solvent, 3-ethoxy-N,N-dimethyl-propionamide can be synthesized.

However, this method is not an inexpensive synthesis method, since raw materials are expensive.

Patent Document 1: JP-A-S49-66623

Patent Document 2: JP-A-H10-279545

An object of the invention is to provide a method which is capable of producing a β-alkoxypropionamide, which is effective as an amide-based organic solvent, at a low cost.

DISCLOSURE OF THE INVENTION

As a result of intensive studies, the inventors have found that a β-alkoxypropionamide can be obtained for a short period of time under moderate conditions if an alkoxypropionic acid ester is allowed to react with an amine in the presence of a basic catalyst or in the presence of a basic catalyst and a polyol.

Furthermore, the inventors have found that a β-alkoxypropionamide can be produced efficiently by allowing an alcohol to be added to an acrylic acid ester, thereby to synthesize an alkoxypropionic acid ester, followed by the above-mentioned amidization reaction. The invention has been made based on this finding.

According to the invention, the following method for producing a β-alkoxypropionamide can be provided.

1. A method for producing a β-alkoxypropionamide shown by the following formula (I) comprising the step of reacting a β-alkoxypropionic acid ester with an amine in the presence of a basic catalyst or in the presence of a basic catalyst and a polyol:

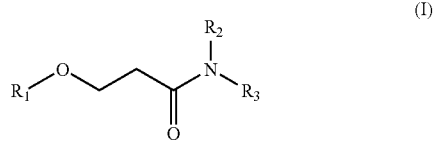

wherein $R_1$ is an alkyl group having 1 to 8 carbon atoms, and $R_2$ and $R_3$ are independently hydrogen, a methyl group, an ethyl group, a methoxy group, an ethoxy group, a methoxymethyl group or a glycidyl group.

2. The method for producing a β-alkoxypropionamide according to 1, further comprising the step of reacting an acrylic ester with an aliphatic alcohol in the presence of a basic catalyst to synthesize the β-alkoxypropionic acid ester.

3. The method for producing a β-alkoxypropionamide according to 2, wherein the β-alkoxypropionic acid ester is synthesized from the acrylic acid ester and the aliphatic alcohol by Michael addition reaction in the presence of the basic catalyst, and subsequently, the β-alkoxypropionic acid ester is reacted with the amine.

4. The method for producing a β-alkoxypropionamide according to 3, wherein the molar ratio of the aliphatic alcohol and the acrylic acid ester (aliphatic alcohol/acrylic acid ester) at the time of charging for the Michael addition reaction is 1.0 to 2.0.

5. The method for producing a β-alkoxypropionamide according to any of 2 to 4, wherein the acrylic ester is a compound shown by the following formula (II):

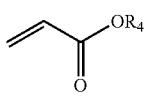

wherein $R_4$ is an alkyl group having 1 to 8 carbon atoms.

6. The method for producing a β-alkoxypropionamide according to any of 2 to 5, wherein the aliphatic alcohol is an aliphatic alcohol having 1 to 8 carbon atoms.

7. The method for producing a β-alkoxypropionamide according to any of 1 to 6, wherein the amine is a compound shown by the following formula (III):

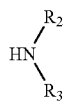

wherein $R_2$ and $R_3$ are independently hydrogen, a methyl group, an ethyl group, a methoxy group, an ethoxy group, a methoxymethyl group or a glycidyl group.

8. The method for producing a β-alkoxypropionamide according to 1, wherein the polyol is ethylene glycol or glycerine.

9. The method for producing a β-alkoxypropionamide according to any one of 1 to 8, wherein $R_1$ is an alkyl group having 1 to 6 carbon atoms.

According to the invention, an alkoxypropionamide can be produced in a high yield under moderate conditions for a short period of time.

In addition, it is possible to allow an acrylic acid ester to react with an aliphatic acid alcohol, both of which are relatively inexpensive, thereby to synthesize an alkoxypropionic acid ester, followed by an amidization reaction. When producing an alkoxypropionamide, these two reaction steps can be performed continuously without separation and purification (deactivation removal of a basic catalyst, separation and purification of an alkoxypropionic acid ester). Therefore, the production method of the invention has a high degree of productivity and is highly significant from an industrial viewpoint.

BEST MODE FOR CARRYING OUT THE INVENTION

The invention is a method for producing a β-alkoxypropionamide shown by the following formula (I), and is characterized in that β-alkoxypropionic acid ester is reacted with an amine in the presence of a basic catalyst or in the presence of a basic catalyst and a polyol.

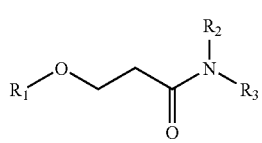

wherein $R_1$ is an alkyl group having 1 to 8 carbon atoms, $R_2$ and $R_3$ are independently hydrogen, a methyl group, an ethyl group, a methoxy group, an ethoxy group, a methoxymethyl group or a glycidyl group.

In the invention, by using a basic catalyst, or a basic catalyst and polyol in combination, at the time of an amidization reaction, an intended product can be obtained in a high yield under moderate conditions for a short period of time. Specifically, an amidization reaction is performed at about 20 to 60° C. for about 2 to 8 hours. If a polyol, such as glycerine, alone is used as in the conventional methods, the reaction temperature and the reaction time become 80 to 120° C. and 20 to 40 hours, respectively. That is, as compared with the production method of the invention, production is required to be performed at higher temperatures for a prolonged period of time.

A β-alkoxypropionic acid ester as a raw material can be synthesized by reacting an acrylic acid ester and an aliphatic alcohol in the presence of a basic catalyst, for example.

As the acrylic acid ester, one shown by the following formula (II) can be given.

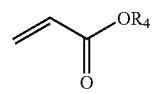

wherein $R_4$ is an alkyl group having 1 to 8 carbon atoms.

Specific examples of the acrylic acid ester shown by the formula (II) include methyl acrylate, ethyl acrylate, n-propyl acrylate, isopropyl acrylate, n-butyl acrylate, isobutyl acrylate, t-butyl acrylate, n-pentyl acrylate, isopentyl acrylate and 2-ethylhexyl acrylate. Of these, one in which $R_4$ is an alkyl group having 1 to 6 carbon atoms is preferable.

As the aliphatic alcohol, an aliphatic alcohol having 1 to 8 carbon atoms can be used. Specifically, methanol, ethanol, n-propanol, isopropanol, n-butanol, sec-butanol, t-butyl alcohol, n-pentanol, isopentanol, n-hexanol, 2-ethylhexanol, or the like can be used. Of these, an aliphatic monovalent alcohol having 1 to 4 carbon atoms is preferable.

A β-alkoxypropionic acid ester can be obtained by subjecting the above-mentioned acrylic acid ester and the aliphatic alcohol to an alcohol addition reaction (Michael addition reaction) by using a basic catalyst.

There are no specific restrictions on the basic catalyst which can be used in the alcohol addition reaction, and either an inorganic base or an organic base can be used.

As the inorganic base, a hydroxide of an alkali metal such as sodium, potassium and lithium or $Na_2CO_3$ or the like can be given.

As the organic base, an alkoxide of the above-mentioned alkali metal, a tertiary amine, pyridine, 4-methylaminopyridine or the like can be given.

As the basic catalyst, an alkoxide of an alkali metal is preferable. In particular, potassium butoxide (KOt-Bu) or sodium methoxide ($NaOCH_3$) is preferable.

The basic catalyst can be used either singly or in a mixture. A basic catalyst which has been diluted with an alcohol may also be used.

The basic catalyst may be used alone or in combination of two or more. There are no restrictions on the amount thereof, and the amount can be selected appropriately according to the type of the raw material, or the like. Generally, the amount can be selected within a range of 0.001 to 0.1 mol, preferably, 0.01 to 0.03 mol, per mole of an acrylic acid ester.

As an amine to be reacted with a β-alkoxypropionic acid ester, one shown by the following formula (III) can be given.

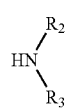

(III)

wherein $R_2$ and $R_3$ are independently hydrogen, a methyl group, an ethyl group, a methoxy group, an ethoxy group, a methoxymethyl group or a glycidyl group.

Of these, dimethylamine or diethylamine are preferable. An amine may be used as it is or after being diluted with an appropriate solvent.

As for the amount ratio of a β-alkoxypropionic acid ester and an amine in an amidization reaction, it is preferred that the amount ratio be a stoichiometric amount ratio, or it is preferred that the amount of an amine be slightly larger. Specifically, the amount ratio of a β-alkoxypropionic acid ester and an amine (amine/ester: molar ratio) is preferably 1 to 3. An amine may be gradually supplied to a reaction system by blowing or the like.

As for the basic catalyst which is used in a reaction in which a β-alkoxypropionic acid ester is amidized, the same catalyst as that used in the above-mentioned alcohol addition reaction (Michael addition reaction) can be used. Of these, an alkoxide of an alkali metal is preferable. In particular, potassium butoxide or sodium methoxide is preferable.

The amount of the catalyst can be appropriately selected according to the type of a raw material or the like. Generally, the amount of the catalyst can be selected within a range of 0.001 to 0.1 mol, preferably, 0.01 to 0.05 mol, per mole of a β-alkoxypropionic acid ester.

If a basic catalyst and a polyol are used in combination, ethylene glycol or glycerine can be preferably used as a polyol. The amount of a polyol is about 0.2 to 2 moles per mole of a β-alkoxypropionic acid ester, preferably within a range of 0.6 to 1.2 moles. Although the conversion ratio slightly decreases by the addition of a polyol, the selectivity for a β-alkoxypropionamide can be improved. If 2 moles or more of a polyol per mole of a β-alkoxypropionic acid ester are added, further improvement in selectivity cannot be attained, and the conversion ratio is lowered, which may prolong the reaction time.

The temperature of an amidization reaction is about 20 to 60° C., and the time of an amidization reaction is about 2 to 8 hours. In the invention, by using a basic catalyst at the time of an amidization reaction, an intended object can be produced in a high yield under such moderate reaction conditions. There are no specific restrictions on the pressure at the time of an amidization reaction. An amidization reaction can be performed without problems under atmospheric pressure.

In the invention, it is preferred that, by Michael addition reaction, a β-alkoxypropionic acid ester be synthesized from an acrylic acid ester and an aliphatic alcohol in the presence of a basic catalyst, then the β-alkoxypropionic acid ester be reacted with an amine (amidization reaction). In the production method of the invention, since removal by deactivation of a basic catalyst and separation and purification of an alkoxypropionic acid ester after Michael addition reaction are not necessary, Michael addition reaction and an amidization reaction can be performed continuously. For this reason, the production process can be simplified, leading to a reduced production cost.

If an amidization reaction is performed immediately after Michael addition reaction, it is preferred that the molar ratio of the aliphatic alcohol and the acrylic acid ester (aliphatic alcohol/acrylic acid ester) during Michael addition reaction be 1.0 to 2.0, particularly preferably, 1.2 to 1.7. If the molar ratio is smaller than 1.0, an unreacted acid ester may remain in Michael addition reaction. As a result, selectivity may be lowered due to the generation of a side-reaction product in a subsequent amidization reaction. If the molar ratio is larger than 2.0, not only the reaction efficiency may be lowered but also the recovered amount of an unreacted alcohol may be increased.

Basic catalysts used in Michael addition reaction and an amidization reaction may be either the same or different. For example, a new basic catalyst may be additionally introduced after the completion of Michael addition reaction. A basic catalyst used in this case may be the same as or different from the catalyst used during Michael addition reaction.

After the completion of the reaction, a basic catalyst may be removed by a neutralization reaction with phosphoric acid or the like.

EXAMPLES

Synthesis of β-Alkoxypropionic Acid Ester:
Reaction (A)

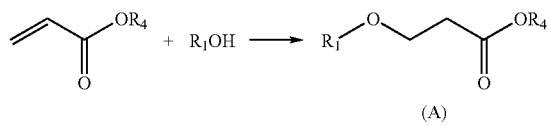

(A)

wherein $R_1$ and $R_4$ are independently a methyl group or a n-butyl group.

Production Example 1

In a 200 ml-four mouth flask provided with a stirrer, a dropping funnel, a Dimroth condenser and a temperature gauge, 30.76 g (0.96 mol) of methanol and 2.24 g (0.02 mol) of potassium t-butoxide (KOt-Bu) as a basic catalyst were added.

74.0 g of methyl acrylate (0.86 mol) was weighed, and added dropwise from the dropping funnel for about one hour. In this case, since heat is generated when a small amount of methyl acrylate is added dropwise, the reaction temperature was controlled to 40° C. by cooling with ice. After the dropwise addition of methyl acrylate, the reaction mixture was stirred with heating at 40° C. for one hour, thereby allowing the total reaction time to be 2 hours.

Thereafter, 2.46 g (0.024 mol) of phosphoric acid (aqueous 85% solution) was added. After confirming that the resulting mixture was neutral by means of pH testing paper, the mixture was stirred for 30 minutes at room temperature.

After the neutralization, suction filtration was performed, whereby a solid product of the neutralized salt of the catalyst was filtered out. Thereafter, the solid product was separated by distillation, whereby methyl β-methoxypropionate was obtained.

The conversion ratio of methyl acrylate after the neutralization was 99 wt %.

As for Production Example 1 and Production Examples 2 to 4, given later, the reaction conditions and the results are shown in Table 1.

TABLE 1

|  |  |  | Production Example 1 | Production Example 2 | Production Example 3 | Production Example 4 |
|---|---|---|---|---|---|---|
| Raw Material Composition | Alcohol | Methanol (mol) | 0.96 | — | 0.96 | 1.29 |
|  |  | n-Butanol (mol) | — | 0.96 | — | — |
|  | Acrylic acid ester | Methyl acrylate (mol) | 0.86 | — | 0.86 | 0.86 |
|  |  | Butyl acrylate (mol) | — | 0.86 | — | — |
|  | Basic catalyst | K(O-tBu) (mol) | 0.02 | 0.02 | — | 0.02 |
|  |  | $NaOCH_3$ (mol) | — | — | 0.02 | — |
| Reaction conditions |  | Temperature (° C.) | 40 | 40 | 40 | 40 |
|  |  | Time (h) | 2 | 2 | 2 | 2 |
|  |  | Pressure (MPa) | Atmospheric pressure | Atmospheric pressure | Atmospheric pressure | Atmospheric pressure |
| Results |  | Ester conversion ratio (wt %) | 99 | 97 | 98 | 100 |

Production Example 2

Synthesis was performed in the same manner as in Production Example 1, except that butyl acrylate was used instead of methyl acrylate and n-butanol was used instead of methanol.

The conversion ratio of butyl acrylate after the neutralization was 97 wt %.

Production Example 3

Synthesis was performed in the same manner as in Production Example 1, except that, as the basic catalyst, 3.86 g (0.02 mol as $NaOCH_3$) of sodium methoxide (28 wt % $NaOCH_3$/methanol solution) was added instead of potassium t-butoxide (KOt-Bu).

The conversion ratio of methyl acrylate after the neutralization was 98 wt %.

Production Example 4

Synthesis was performed in the same manner as in Production Example 1, except that the amount of methanol was increased from 0.96 mol to 1.29 mol.

The conversion ratio of methyl acrylate after the neutralization was 100 wt %.

Synthesis of Alkoxypropioamide: Reaction (B)

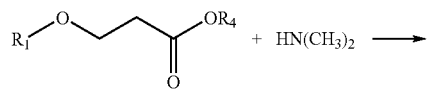

-continued

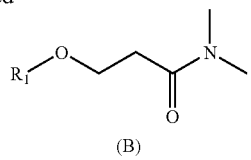

wherein $R_1$ and $R_4$ are independently methyl.

Example 1

To a 200 ml-four mouth flask placed under a dry air stream, 70.88 g (0.6 mol) of methyl β-methoxypropionate and 1.12 g (0.01 mol) of potassium t-butoxide (KOt-Bu) as the basic catalyst were added.

At room temperature (about 20° C.), while blowing a dimethyamine gas continuously by means of a capillary tube in an amount which was slightly larger than the amount absorbed during the reaction, the reaction was conducted for 4 hours with stirring under atmospheric pressure. After the start of blowing dimethylamine, the reaction temperature was elevated to 40° C., at the highest.

After the reaction, the reaction liquid was neutralized with phosphoric acid (aqueous 85% solution), and the catalyst was removed. Using the solution containing an intended product, the conversion ratio and the selectivity were confirmed by means of gas chromatography (GC).

The conversion ratio of methyl β-methoxypropionate was 95 wt % and the selectivity for the β-methoxy-N,N-dimethylpropionamide was 67 wt %.

As for Example 1, Examples 2 to 4 and Comparative Examples 1 and 2, given later, the reaction conditions and the results are shown in Table 2.

TABLE 2

|  |  |  | Example 1 | Example 2 | Example 3 | Example 4 | Comparative Example 1 | Comparative Example 2 |
|---|---|---|---|---|---|---|---|---|
| Raw material composition | Alkoxy propionic acid ester | Methyl β-methoxypropionate (mol) | 0.6 | 0.6 | 0.6 | 0.6 | 0.6 | 0.6 |
|  | Dimethylamine | Charged amount (mol) | Circulating system | 0.9 | 0.9 | 0.9 | Circulating system | Circulating system |
|  |  | Charging method | Gas blow | Autoclave | Autoclave | Autoclave | Gas blow | Gas blow |
|  | Basic catalyst | K(O-tBu) (mol) | 0.01 | 0.019 | — | — | — | — |
|  |  | $NaOCH_3$ (mol) | — | — | 0.019 | 0.019 | — | — |
|  | Polyol | Glycerin (mol) | — | — | — | 0.48 | 0.4 | — |
|  |  | Ethylene glycol (mol) | — | — | 0.48 | — | — | 0.4 |

TABLE 2-continued

|  |  | Example 1 | Example 2 | Example 3 | Example 4 | Comparative Example 1 | Comparative Example 2 |
|---|---|---|---|---|---|---|---|
| Reaction conditions | Temperature (° C.) | 20~40 | 20~40 | 60 | 60 | 80 | 80 |
|  | Time (h) | 4 | 4 | 8 | 8 | 20 | 20 |
|  | Pressure (MPa) | Atmospheric pressure | 0.08 | 0.08 | 0.08 | Atmospheric pressure | Atmospheric pressure |
| Results | Selectivity (wt %) | 67 | 74 | 89 | 86 | 51 | 62 |
|  | Ester conversion ratio (wt %) | 95 | 98 | 88 | 85 | 46 | 54 |

Example 2

To a 300 ml-autoclave provided with a stirrer, 70.88 g (0.6 mol) of methyl β-methoxypropionate and 2.13 g (0.019 mol) of potassium t-butoxide (KOt-Bu) as the basic catalyst were added.

Thereafter, while cooling the autoclave, 40.6 g (0.9 mol) of dimethylamine was added from a dimethylamine cylinder. The pressure at which the autoclave was filled with dimethylamine and the temperature was cooled to room temperature was 0.08 MPa.

The reaction was conducted with stirring at room temperature for 4 hours.

The conversion ratio of methyl β-methoxypropionate was 98 wt % and the selectivity for β-methoxy-N,N-dimethylpropionamide was 74 wt %.

Example 3

A reaction was conducted in the same manner as in Example 2, except that 1.03 g (0.019 mol) of sodium methoxide (NaOCH$_3$) as the basic catalyst was added, 29.8 g (0.48 mol) of ethylene glycol as a polyol were added, the reaction temperature was changed to 60° C. and the reaction time was changed to 8 hours.

The conversion ratio of methyl β-propionate was 88 wt % and the selectivity for β-methoxy-N,N-dimethylpropionamide was 89 wt %.

Example 4

A reaction was conducted in the same manner as in Example 3, except that 44.2 g (0.48 mol) of glycerin was added as the polyol.

The conversion ratio of methyl β-methoxypropionate was 85 wt % and the selectivity for β-methoxy-N,N-dimethylpropionamide was 86 wt %.

Comparative Example 1

To a 200 ml-four mouth flask placed under a dry air stream, 70.88 g (0.6 mol) of methyl β-methoxypropionate and 36.8 g (0.4 mol) of glycerine having a function of a catalyst and a solvent were added. The resultant was heated to 80° C. under atmospheric pressure. While continuously blowing a dimethylamine gas, a reaction was conducted for 20 hours.

The conversion ratio of methyl β-methoxypropionate was 46 wt % and the selectivity for β-methoxy-N,N-dimethylpropionamide was 51 wt %.

Comparative Example 2

A reaction was conducted in the same manner as in Comparative Example 1, except that 0.4 mol of ethylene glycol was added as the polyol.

The conversion ratio of methyl β-methoxypropionate was 54 wt % and the selectivity for β-methoxy-N,N-dimethylpropionamide was 62 wt %.

[Continuous Synthesis]

In the following examples, β-alkoxypropionic acid ester was synthesized from an acrylic acid ester according to the following formula. Immediately after, a dimethylamine gas was blown thereto, whereby a β-alkoxypropionamide was synthesized.

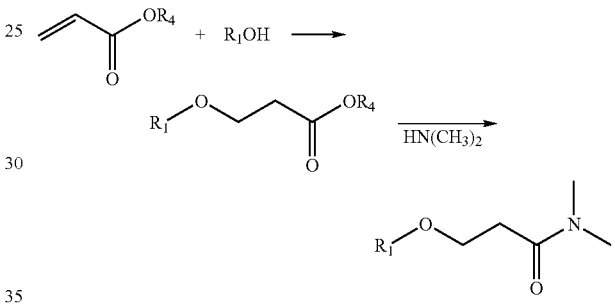

wherein $R_1$ and $R_4$ are independently a methyl group.

Example 5

In a 200 ml-four mouth flask provided with a stirrer, a dropping funnel, a Dimroth condenser and a temperature gauge, 41.33 g (1.29 mol) of methanol and 1.30 g (0.024 mol) of sodium methoxide as the basic catalyst were added.

74.04 g of methyl acrylate (0.86 mol) was weighed, and added gradually from the dropping funnel. In this case, since heat is generated when a small amount of methyl acrylate is added dropwise, the reaction temperature was controlled to 40° C. by cooling with ice. After the dropwise addition for 1 hour, the reaction was conducted for 1 hour.

Thereafter, 0.39 g (0.007 mol) of sodium methoxide was added at room temperature (about 20° C.). Then, a dimethylamine gas was blown by a circulating system. The reaction was conducted for 4 hours under atmospheric pressure. After the start of blowing dimethylamine, the reaction temperature was elevated to 50° C., at the highest.

After the reaction, the liquid was taken out of the flask and neutralized by adding 2.46 g (0.024 mol) of phosphoric acid (aqueous 85% solution).

After the neutralization, suction filtration was performed, whereby a solid product of a neutralized salt of the catalyst was filtered out. As a result, a solution of a β-methoxy-N,N-dimethylpropionamide as an intended product was obtained. As a result of a GC analysis of this solution, it was found that the conversion ratio of methyl acrylate was 98 wt % and the selectivity for β-methoxy-N,N-dimethylpropionamide was 80 wt %.

As for Example 5, and Examples 6 to 8, given later, the reaction conditions and the results are shown in Table 3.

TABLE 3

|  |  |  | Example 5 | Example 6 | Example 7 | Example 8 |
|---|---|---|---|---|---|---|
| Michael addition reaction | | | | | | |
| Raw material Composition (mol) | Alcohol | Methanol | 1.29 | 1.29 | 1.29 | 0.86 |
|  | Acrylic acid ester | Methyl acrylate | 0.86 | 0.86 | 0.86 | 0.86 |
|  | Basic catalyst | $NaOCH_3$ | 0.024 | 0.024 | 0.024 | 0.024 |
|  |  | Temperature (° C.) | 40 | 40 | 40 | 40 |
|  |  | Time (h) | 2 | 2 | 2 | 2 |
|  |  | Pressure (MPa) | Atmospheric pressure | Atmospheric pressure | Atmospheric pressure | Atmospheric pressure |
| Amidization reaction | | | | | | |
| Raw material Composition (mol) | Dimethylamine | Charging amount | Circulating system | Circulating system | Circulating system | Circulating system |
|  |  | Charging method | Gas blow | Gas blow | Gas blow | Gas blow |
|  | Basic catalyst | $NaOCH_3$ | 0.007 | 0.007 | 0.007 | — |
|  | Polyol | Glycerin | — | — | 0.7 | — |
|  |  | Ethylene glycol | — | 0.7 | — | — |
|  | Reaction conditions | Temperature(° C.) | 20~50 | 60 | 60 | 20~47 |
|  |  | Time (h) | 4 | 4 | 4 | 4 |
|  |  | Pressure (MPa) | Atmospheric pressure | Atmospheric pressure | Atmospheric pressure | Atmospheric pressure |
|  | Results | Selectivity (wt %) | 80 | 95 | 92 | 62 |
|  |  | Ester conversion ratio (wt %) | 98 | 98 | 95 | 91 |

Example 6

A reaction was conducted in the same manner as in Example 5, except that 0.39 g (0.007 mol) of sodium methoxide and 43.4 g (0.7 mol) of ethylene glycol as the polyol were added at the time of the amidization reaction before blowing dimethylamine and the reaction temperature was changed to 60° C.

The conversion ratio of methyl acrylate was 98 wt % and the selectivity for β-methoxy-N,N-dimethylpropionamide was 95 wt %.

Example 7

A reaction was conducted in the same manner as in Example 6, except that 0.39 g (0.007 mol) of sodium methoxide and 64.5 g (0.7 mol) of glycerine as the polyol were added at the time of the amidization reaction before blowing dimethylamine.

The conversion ratio of methyl acrylate was 95 wt % and the selectivity for β-methoxy-N,N-dimethylpropionamide was 92 wt %.

Example 8

A reaction was conducted in the same manner as in Example 5, except that the amount of methanol was changed to 27.55 g (0.86 mol) and sodium methoxide was not added at the time of the amidization reaction, whereby β-methoxy-N,N-dimethylpropionamide was obtained.

The conversion ratio of methyl acrylate was 91 wt % and the selectivity for β-methoxy-N,N-dimethylpropionamide was 62 wt %.

INDUSTRIAL APPLICABILITY

According to the production method of the invention, a β-alkoxypropionamide can be obtained in a high yield under moderate conditions for a short period of time. In addition, since a β-alkoxypropionamide can be produced efficiently from an acrylic acid ester and an aliphatic alcohol, which are relatively inexpensive, the production method of the invention is very effective as a method for producing a β-alkoxypropionamide.

The invention claimed is:

1. A method for producing a β-alkoxypropionamide of formula (I) comprising reacting a β-alkoxypropionic acid ester with an amine in the presence of a basic catalyst and a polyol:

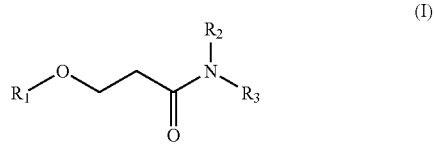

(I)

wherein $R_1$ is an alkyl group having 1 to 8 carbon atoms, and $R_2$ and $R_3$ are independently hydrogen, a methyl group, an ethyl group, a methoxy group, an ethoxy group, a methoxymethyl group or a glycidyl group.

2. The method for producing a β-alkoxypropionamide according to claim 1, further comprising reacting an acrylic acid ester with an aliphatic alcohol in the presence of a basic catalyst to synthesize the β-alkoxypropionic acid ester.

3. The method for producing a β-alkoxypropionamide according to claim 2, wherein the β-alkoxypropionic acid ester is synthesized from the acrylic acid ester and the aliphatic alcohol by a Michael addition reaction in the presence of the basic catalyst, and subsequently, the β-alkoxypropionic acid ester is reacted with the amine.

4. The method for producing a β-alkoxypropionamide according to claim 3, wherein the molar ratio of the aliphatic alcohol and the acrylic acid ester (aliphatic alcohol/acrylic acid ester) at the time of charging for the Michael addition reaction is 1.0 to 2.0.

5. The method for producing a β-alkoxypropionamide according to claim 2, wherein the acrylic ester is a compound of formula (II):

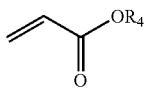
(II)

wherein R₄ is an alkyl group having 1 to 8 carbon atoms.

6. The method for producing a β-alkoxypropionamide according to claim 2, wherein the aliphatic alcohol is an aliphatic alcohol having 1 to 8 carbon atoms.

7. The method for producing a β-alkoxypropionamide according to claim 1, wherein the amine is a compound of formula (III):

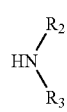
(III)

wherein R₂ and R₃ are independently hydrogen, a methyl group, an ethyl group, a methoxy group, an ethoxy group, a methoxymethyl group or a glycidyl group.

8. The method for producing a β-alkoxypropionamide according to claim 1, wherein the polyol is ethylene glycol or glycerine.

9. The method for producing a β-alkoxypropionamide according to claim 1, wherein $R_1$ is an alkyl group having 1 to 6 carbon atoms.

10. The method for producing a β-alkoxypropionamide according to claim 1, wherein said reaction is performed at about 20 to 60° C. for about 2 to 8 hours.

11. The method for producing a β-alkoxypropionamide according to claim 1, wherein said basic catalyst is at least one selected from the group consisting of a hydroxide of an alkali metal, an alkoxide of an alkali metal, a tertiary amine, pyridine and 4-methylaminopyridine.

12. The method for producing a β-alkoxypropionamide according to claim 1, wherein said basic catalyst is at least one selected from the group consisting of NaOH, KOH, LiOH and $Na_2CO_3$.

13. The method for producing a β-alkoxypropionamide according to claim 1, wherein said basic catalyst is at least one selected from the group consisting of potassium t-butoxide and sodium methoxide.

14. The method for producing a β-alkoxypropionamide according to claim 1, wherein said basic catalyst is present in an amount of 0.001 to 0.1 mole per mole of acrylic acid ester.

15. The method for producing a β-alkoxypropionamide according to claim 1, wherein said polyol is used in an amount of 0.2 to 2 moles per mole of β-alkoxypropionic acid ester.

16. The method for producing a β-alkoxypropionamide according to claim 1, wherein said polyol is used in an amount of 0.6 to 1.2 moles per mole of β-alkoxypropionic acid ester.

* * * * *